United States Patent [19]

Oka et al.

[11] Patent Number: 4,916,063

[45] Date of Patent: Apr. 10, 1990

[54] BU-2867T PEPTIDE ANTIBIOTICS

[75] Inventors: Masahisa Oka, Yokohama; Masataka Konishi, Kawasaki, both of Japan

[73] Assignee: Bristol-Myers Company, New York, N.Y.

[21] Appl. No.: 95,722

[22] Filed: Sep. 14, 1987

Related U.S. Application Data

[62] Division of Ser. No. 908,850, Sep. 18, 1986, Pat. No. 4,777,160.

[51] Int. Cl.⁴ .................... C12P 21/04; C12P 17/10; C12N 1/00
[52] U.S. Cl. .................. 435/71.3; 435/121; 435/852.1; 435/82.2
[58] Field of Search .................. 435/121.70, 71, 253, 435/822; 530/317

[56] References Cited

U.S. PATENT DOCUMENTS 3,651,216  3/1972  Ringel et al. .................. 435/171

*Primary Examiner*—Charles F. Warren
*Assistant Examiner*—Irene Marx
*Attorney, Agent, or Firm*—David M. Morse

[57] ABSTRACT

Novel peptide antibiotics designated herein as BU-2867T F and G are produced by fermentation of *Polyangium brachysporum* strain K481-B101 (ATCCC 53080). The new antibiotics are found to have antifungal activity and to inhibit P388 lymphatic leukemia in rodents.

2 Claims, 2 Drawing Sheets

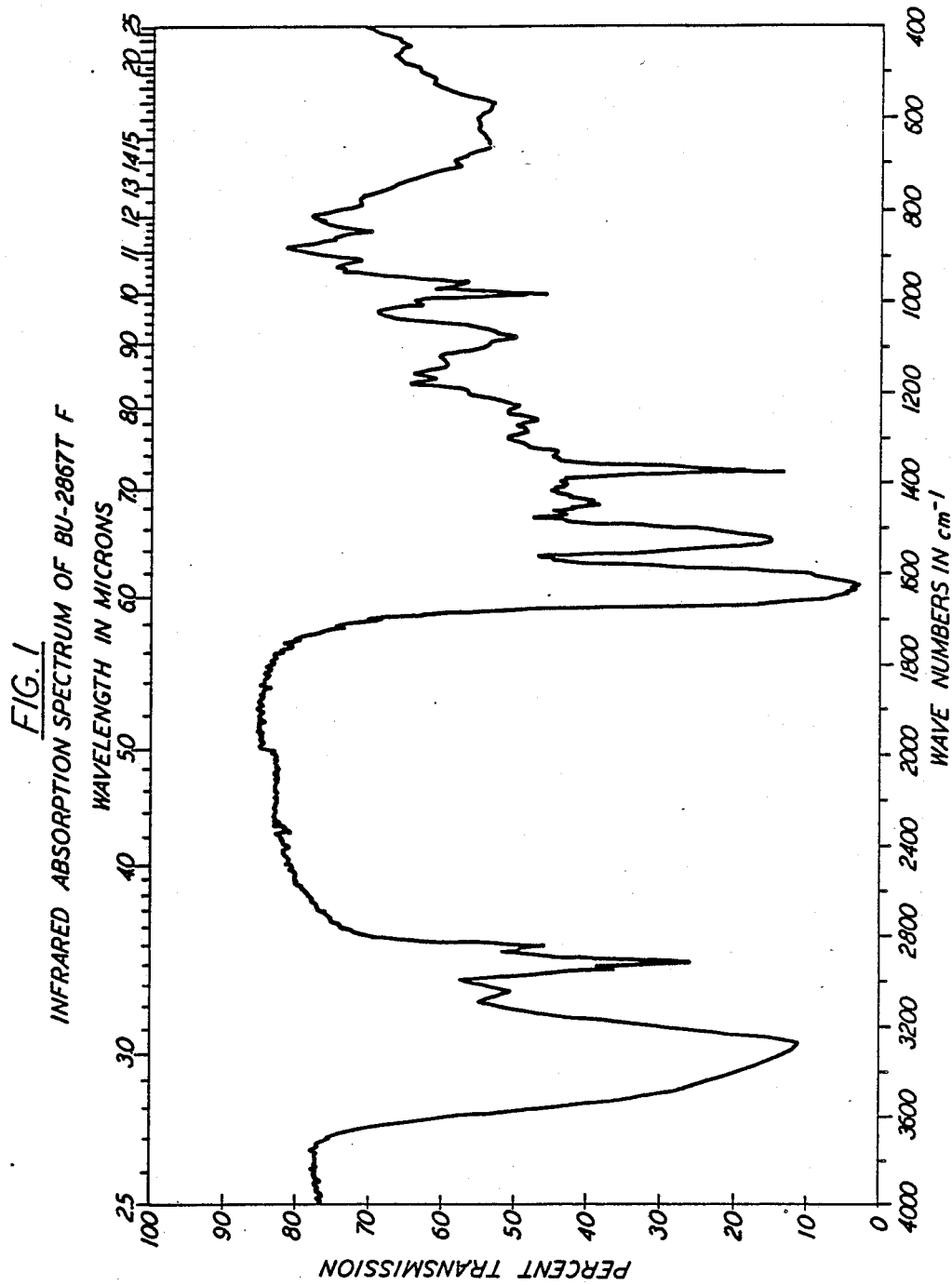

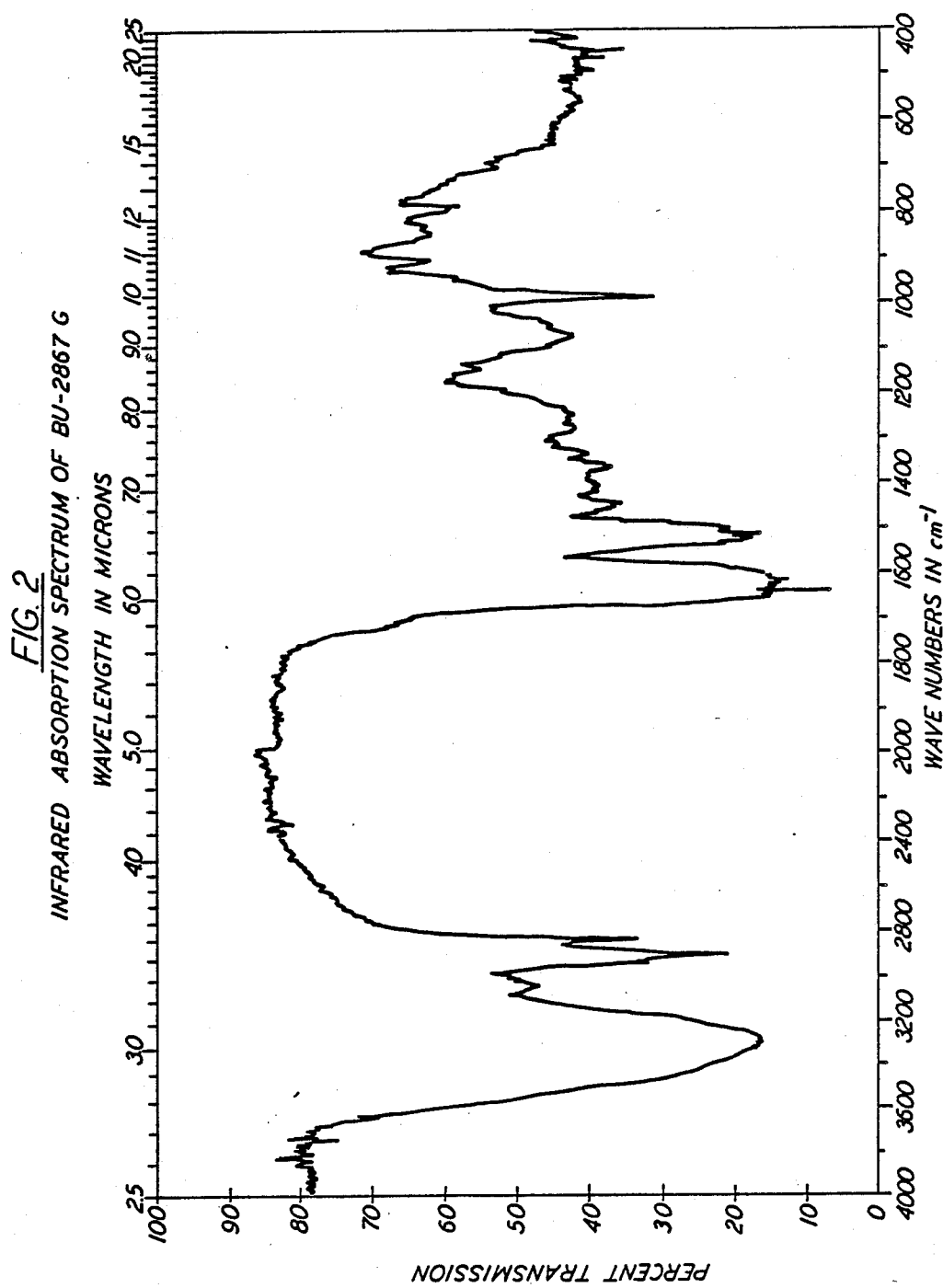
FIG. 2 INFRARED ABSORPTION SPECTRUM OF BU-2867 G

BU-2867T PEPTIDE ANTIBIOTICS

CROSS-REFERENCE TO RELATED APPLICATIONS

This is a division of our co-pending application Ser. No. 908,850 filed Sept. 18, 1986, now U.S. Pat. No. 4,777,160.

BACKGROUND OF THE INVENTION

1. Field of the Invention

This invention relates to novel peptide antibiotics and to their use as antimicrobial and antitumor agents. The invention also relates to production of the new peptide antibiotics by fermentation.

2. Description of the Prior Art

U.S. patent application Ser. No. 771,090 filed Aug. 30, 1985 and its continuation-in-part application Ser. No. 855,649 filed Apr. 25, 1986 disclose novel peptide antibiotics of the formula

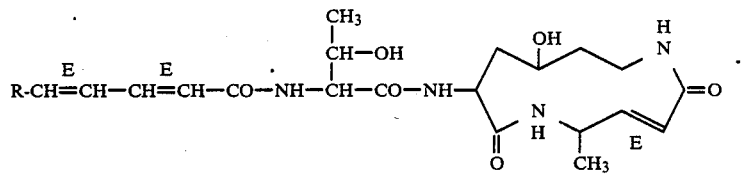

wherein R is $CH_3(CH_2)_6-$, $CH_3-(CH_2)_4-CH=CH(CH_2)_2-$ or $CH_3-(CH_2)_8-$ which are produced by fermentation of *Polyangium brachysporum* sp. nov., strain K481-B101 (ATCC 53080). The above-mentioned peptide antibiotics are disclosed as having both antifungal and antitumor activity.

SUMMARY OF THE INVENTION

The present inventors in further investigation of the fermentation of *Polyangium brachysporum* strain K481-B101 (ATCC 53080) have discovered two additional novel peptide antibiotics which also have antifungal and antitumor activity. Accordingly, the present invention provides novel peptide antibiotics of the formulae

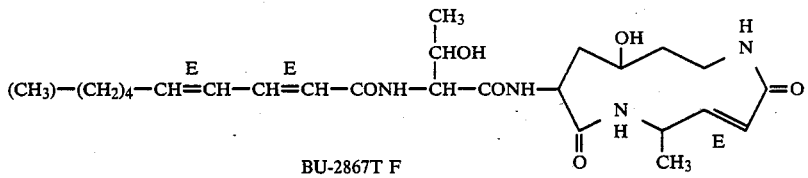

BU-2867T F and

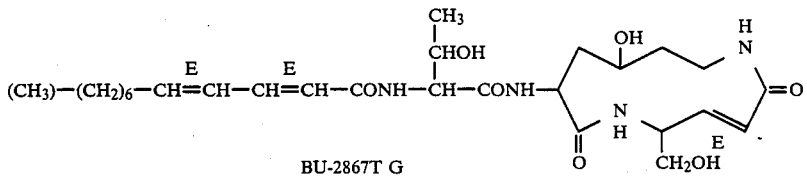

BU-2867T G

In a further aspect the invention provides a process for the preparation of BU-2867T F and BU-2867T G, said process comprising cultivating *Polyangium brachysporum* sp. nov. strain K841-B101 (ATCC 53080), or a BU-2867T F- or G-producing mutant thereof, in an aqueous nutrient medium containing assimilable sources of nitrogen and carbon under submerged aerobic conditions until a substantial amount of BU-2867T F and/or G is produced by said organism in said culture medium and then recovering the BU-2867T F and/or G component(s) from the culture medium substantially free of co-produced substances.

DESCRIPTION OF THE DRAWINGS

FIG. 1 shows the infrared absorption spectrum of BU-2867T F (KBr pellet).

FIG. 2 shows the infrared absorption spectrum of BU-2867T G (KBr pellet).

DETAILED DESCRIPTION

The BU-2867T F and G antibiotics of the present invention may be prepared by fermentation of a new species of the genus Polyangium. Such species is proposed to be designated *Polyangium brachysporum* sp. nov. and a description of strain K481-B101, the isolate employed as the producing organism, is provided below.

THE MICROORGANISM

The morphological, cultural and physiological characterization of K481-B101 was made by the methods described by McCurdy, Jr. H. D.: Studies on the Taxonomy of the Myxobacterales. II, Polyangium and the demise of the Sorangiaceae. Intl. J. Syst. Bacteriol. 20: 283–296, 1970; Reichenbach, H.: *Nannocystis exedens* gen. nov., sp. nov., a new myxobacterium of the family Sorangiaceae. Arch. Mikrobiol. 70: 119–138, 1970; Christensen, P. and F. D. Cook: Lysobacter, a new Genus of nonfruiting, gliding bacteria with a high base ratio. Intl. J. Syst. Bacteriol. 28: 367–393, 1978; and Christensen, P.: Synonymy of *Flavobacterium pectinovorum* Dorey with *Cytophaga johnsonae* Stanier. Intl. J. Syst. Bacteriol. 27: 122–132, 1977. Maintenance and purification was by the procedures described by Peterson, J. E.: Isolation, cultivation and maintenance of the myxobacteria. Methods in Microbiology 3B: 185–210, 1969. Edit. J. R. Norris and D. w. Ribbons. Academic Press (London and New York); and Reichenbach, H. and M. Dworkin: The Order Mixobacterales. The Prokaryotes. Volume I: 328–355, 1981. Edit. M. P. Starr et al. Springer-Verlag (Berlin, Heidelberg and New York). The taxonomic position was determined according to the description in Bergey's Manual, 8th Ed., 1974 and "The Prokaryotes, Vol. I".

MORPHOLOGY

Casitone-Mg$^{++}$ agar, chitin agar, yeast cell agar and rabbit dung pellet-water agar were used for the morphological study. K481-B101 is a Gram-negative, non-flagellate bacterium. The vegetative cells are cylindrical (0.6–0.8 by 2–10 micrometers) with blunt rounded ends. The vegetative cells show flexible and slow gliding movements on moist surface of agar medium or soft agat medium. Myxospores differ clearly from vegetative cells, are oval or spherical, 0.6–0.8 by 0.6–1.5 micrometers, non-refractile or refractile, and occasionally pair. K481-B101 forms on most descriptive agar media sessile sporangia enveloping myxospores. The sporangia are oval, spherical or pillow-like, fairly variable in size, 12×20 to 80×120 micrometers, often bounded by a common envelope or slimy layer, double contoured, and occur singly on in clusters (sori). The morphology of K481-B101 is represented in Table 1.

CULTURAL CHARACTERISTICS

K481-B101 grow moderately on casitone-Mg$^{++}$ agar (McCurdy, 1969) and yeast cell agar (Christensen and Cook, 1978), but poorly on Bacto-nutrient agar or Bacto-heart infusion agar. Rhizoid or feathery swarmings are observed on YP-soft agar (yeast extract 0.3%, peptone 0.1%, NaCl 0.01%, Agar 0.3%, pH 6.6–6.8), but not on casitone-Mg$^{++}$ agar. The colonies on casitone-Mg$^{++}$ agar are circular, translucent and pale greenish yellow, and weakly etch, erode or penetrate into agar. The cultural characteristics are shown in Table 2.

PHYSIOLOGICAL CHARACTERISTICS

K481-B101 hydrolyzes starch, chitin, gelatin and casein, but not cellulose and agar. It lyses autoclaved yeast cell, but not living cell or *Micrococcus luteus*. K481-B101 is mesophilic, and sensitive to 2% NaCl. The physiological characteristics are shown in Table 3.

CONCOMITANCE OF FLAGELLATE BACTERIA AND OCCURRENCE OF SPONTANEOUS VARIANT

Concomitance of Gram-negative, rod-shaped flagellate bacteria was observed in the original culture. K481-B101 was fairly well purified by combining the usual techniques of dilution and single cell isolation with sonication, heat shock treatment or antibiotic sensitivity (e.g. pipemidic acid at 50 mcg/ml) using the myxospore or fruiting body. Unpurified culture of K481-B101 occurred mucoid variants which form whitish dome-shaped colony with swarming halo. The vegetative cells of these mucoid variants are somewhat larger than the parental strain, and measured 0.8–1.0×2.0–3.5 micrometers. The cluster of sporangia (sorus) is predominantly formed by mucoid variants.

TAXONOMIC POSITION

K481-B101 is a fruiting gliding bacterium, isolated from a soil sample. The diagnostic major characteristics of the strain are as follows:
Vegetative cells:
(1) cylindrical, of uniform diameter
(2) not tapered at ends
(3) penetrable into agar media
(4) Congo red, not adsorbed
Myxospores:
(1) differentiated from vegetative cells
(2) oval or spherical
(3) non-refractile or refractile
Sporangia:
(1) sessile
(2) oval, spherical or irregular
(3) often bounded by a common envelope of slimy layer
(4) double contoured
(5) pale yellow (lack of distinct color)
(6) occurring singly or in clusters (sori)
Cultural and Physiological Characteristics:
(1) colony, golden yellow to whitish
(2) colonies, weakly etch, erode and penetrate agar
(3) chitinolytic but not cellulolytic
(4) yeast cell lyzed, but *Micrococcus luteus* not lyzed The above-mentioned morphological, cultural and physiological characteristics of K481-B101 indicate that K481-B101 is classified into the order Myxobacterales. Among the genera of Myxobacterales, the general Myxococcus, Archangium and Cystobacter are differentiated from K481-B101 on account of the tapered vegetative cells and the fruiting body morphology. The genera Melittangium, Stigmatella and Chondromyces differ from K481-B101 in the stalked sporangia.

K481-B101 is similar to the general Polyangium and Nannocystis. K481-B101 resembles the genus Nannocystis in the formations of oval or spherical myxospores, and oval or spherical, solitary sporangia, but differs from the latter in the cylindrical vegetative cells of uniform diameter and the lack of ability to etch, erode and penetrate into agar. K481-B101 resembles the genus Polyangium in the cylindrical vegetative cells with blunt rounded ends, the predominant formation of non-refractile myxospores and the oval or spherical, double contoured sporangia. Based on the results of comparative studies with the general of Order Myxobacterales, K481-B101 is considered to be classified as a species of the genus Polyangium. Among the species of Polyangium, *P. luteum* is similar to K481-B101 in the size of vegetative cells, the color and shape of sporangia and the color of vegetative colony. However, K481-B101 differs from *P. luteum* in the oval of spherical myxospores which are much contracted and the lack of ability to lyze bacterial living cells such as the cells of *Micrococcus luteus*.

Thus, K481-B101 is concluded to be a new species of the genus Polyangium in the family Polyangiaceae, the Order Myxobacterales, and is proposed to be designated *Polyangium brachsporum* sp. nov. The type strain is No. K481-B101 (single isolate), and the culture has been deposited in the American Type Culture Collection with the accession number ATCC 53080.

TABLE 1

| Morphology of K481-B101 | |
|---|---|
| Vegetative cells: | Gram-negative. Cylindrical with blunt rounded ends, (0.6–0.8 by 2.0–10 micrometers). Congo red, not adsorbed. |
| Myxospores: | Distinguishable from vegetative cells. Much shrunken, becoming oval or spherical, 0.6–0.8 by 0.6–1.5 micrometers, non-refractile. Longer |

TABLE 1-continued

| Morphology of K481-B101 | |
|---|---|
| Sporangia: | incubation affords refractile ones. Sessile, occurring singly or in clusters. Oval, spherical, pillow-shaped or shapeless. Considerably variable in size, 12 × 20 to 80 × 120 micrometers. Bounded by a common envelope or slimy layer. Double contoured. Embedded in agar. Clusters of two to ten or more sporangia range 50 to 300 micrometers in size of total mass. |
| Microcolony: | On chitin agar after incubation for 2 weeks. Palisade or zigzag arrangement of chains of vegetative cells at periphery. Gliding movement of single cells is observed, but that of cell masses is not seen. |

TABLE 2

| Cultural characteristics of K481-B101 Colony on casitone-$Mg^{++}$ agar (McCurdy, 1969) at 28° C. for 6 days | |
|---|---|
| Form: | circular |
| Surface: | smooth, later partially wrinkled |
| Elevation: | raised |
| Edge: | entire or somewhat irregular, and absence of distinct protrusion such as shapes of tongue, feather or rhizoid |
| Optical property: | semi-transparent or opaque |
| Color of colony: | pale greenish yellow |
| Diffusible pigment: | none |

GROWTH ON CHITIN AGAR AFTER INCUBATION AT 28° C. FOR 3 WEEKS

Thin, translucent, pale yellow or colorless. Thick, opaque and yellowish-white at peripheral part. Concentric formation of sporangia at the periphery. Weakly etch, erode or penetrate the agar.

TABLE 3

| Physiological characteristics of K481-B101 | |
|---|---|
| Hydrolysis of | |
| Soluble starch | + |
| Potato starch | + |
| CMC sodium | + |
| Cellulose | − |
| Agar | − |
| Chitin | + |
| Alginate sodium | − |
| Polypectate sodium | − |
| Gelatin | + |
| Casein | + |
| Growth on | |
| Simon's citrate agar | − |
| Christensen citrate agar | − |
| Glucose-ammonium salts agar | − |
| Asparagin-ammonium salts agar | + |
| Production of | |
| Indole | − |
| $H_2S$ | + |
| Acetoin (VP-reaction) | − |
| Urease | + |
| Oxidase | + |
| Catalase | + |
| Lytic Action to | |
| Living cell *Micrococcus luteus* strains PCI 1001 & ATCC 9341 | − |
| Autoclaved yeast cell | + |
| Reactions | |
| Milk coagulation: | − |
| Milk peptonization: | + |
| NaCl tolerance: | Growth: 1.0% NaCl or less |

TABLE 3-continued

| Physiological characteristics of K481-B101 | |
|---|---|
| | No growth: 2.0% NaCl or more |
| pH tolerance: | Growth range: pH 5.5–10.5 Scant growth: pH 5.0 No growth: pH 4.5 and 11.5 |
| Growth temperature: | Maximal growth: 37° C. Growth range: 15° C.–42° C. No growth: 10° C. and 45° C. |
| Oxidative or fermentative: reaction | Oxidative (Hugh and Leifson medium) |

ANTIBIOTIC PRODUCTION

BU-2867T F and G may be produced by cultivating a BU-2867T F- and/or G-producing strain of *Polyangium brachysporum* having the characteristics of ATCC 53080 or a BU-2867T F- and/or G-producing mutant thereof under submerged aerobic conditions in an aqueous nutrient medium. The organism is grown in a nutrient medium containing an assimilable carbon source, for example an assimilable carbohydrate. Examples of preferred carbon sources include lactose, glycerol, sucrose, corn starch, glucose, mannose and fructose. When starch is used as the carbon source in the nutrient medium, amylase may be added to the broth before harvest to reduce any emulsion problems which may occur. The nutrient medium should also contain an assimilable nitrogen source such as, for example, fish meal, peptone, soybean flour, peanut meal, cotton seed meal and corn steep liquor. Nutrient inorganic salts may also be incorporated in the medium and such salts may comprise any of the usual salts capable of providing sodium, potassium, ammonium, calcium, phosphate, sulfate, chloride, bromide, nitrate, carbonate or like ions.

Production of the new BU-2867T antibiotics can be effected at any temperature conducive to satisfactory growth of the organism, i.e. approximately 15° C.–42° C., and is conveniently carried out at a temperature of around 28° C. Ordinarily, optimum production is obtained after incubation periods of about 40 hours in a 20 liter fermentation vessel. The fermentation may be carried out in Erlenmeyer flasks and in laboratory or industrial fermenters of various capacities. When tank fermentation is to be carried out, it is desirable to produce a vegetative inoculum in a nutrient broth by inoculating the broth culture with a slant or soil culture or a lyophilized culture of the organism. After obtaining an active inoculum in this manner, it is transferred aseptically to the fermentation tank medium for large scale production of the antibiotics. The medium in which the vegetative inoculum is produced can be the same as, or different from, that utilized in the tank for the production of the new antibiotics, as long as it is such that a good growth of the microorganism is obtained.

It is to be understood that for the production of BU-2867T F and G, the present invention, though described in detail with reference to the strain of *Polyangium brachysporum* K481-B101 (ATCC 53080), is not limited to this microorganism or to microorganisms fully described by the cultural characteristics disclosed herein. It is intended that this invention also include other BU-2867T F- and G-producing strains or mutants of the deposited microorganism which can be produced by methods well-known to those skilled in the art, e.g. by subjecting the deposited microorganism to X-ray or ultraviolet radiation, nitrogen mustard, phage exposure, or the like.

When the fermentation is complete, the antibiotic complex is extracted from the culture broth with a suitable organic solvent or mixture thereof such as a mixture of n-butanol and methanol. The organic extract is concentrated and the solid antibiotic complex is precipitated by dilution of the concentrated extract with a suitable antisolvent such as acetone.

Separation of the so-produced complex into the purified BU-2867T F and G components of the present invention may be carried out by conventional chromatographic procedures such as illustrated in Example 2 which follows.

PHYSICO-CHEMICAL PROPERTIES

Both BU-2867T F and G were isolated in the form of white amorphous powders. They were readily soluble in methanol, n-butanol and dimethyl sulfoxide, slightly soluble in chloroform, acetonitrile and ethyl acetate but insoluble in n-hexane and water. The two new components are positive to Rydon-Smith, iodine and sulfuric acid reactions, but negative to ninhydrin, Sakaguchi, anthrone and Dragendorff tests. The molecular formulae of BU-2867T F and G were determined to be $C_{25}H_{40}N_4O_6$ and $C_{27}H_{44}N_4O_7$, respectively, by their mass and $^{13}C$-NMR spectra. The UV spectra of the new components showed single absorption at 260 nm suggesting an $\alpha, \beta, \gamma, \delta$-unsaturated carbonyl group. Their IR spectra (FIG. 1 and #2) indicated the amide carbonyl absorption at 1640 and 1530 cm$^{-1}$. Characterizing properties of the new antibiotics are shown below in Table 4.

TABLE 4
Physico-Chemical Properties of BU-2867T F and G

| | BU-2867T F | BU-2867T G |
|---|---|---|
| Nature | White powder | White powder |
| M.P. (dec.) | 233° C. | 217° C. |
| $[\alpha]_D^{27°}$ (MeOH) | $-113°$(c,0.5) | $-90°$(c,0.25) |
| Molecular formula | $C_{25}H_{40}N_4O_6$ | $C_{27}H_{44}N_4O_7$ |
| EI-MS m/z | 576 (diacetate) | 662 (triacetate) |
| UV $\lambda_{max}^{MeOH}$ nm($E_{1\ cm}^{1\%}$) | 260(474) | 257(668) |
| IR $\nu_{max}^{KBr}$ cm$^{-1}$ | 3300,1640,1530 | 3300,1640,1530 |
| TLC, Silanized, Rf EtOH-H$_2$O (55:45) | 0.50 | 0.43 |
| HPLC, SSC-ODS262, Rt MeOH-H$_2$O (4:1) | 2.8 | 4.4 |

STRUCTURE DETERMINATION

The physico-chemical properties of BU-2867T F and G were very similar to those of the major components BU-2867T A, B and C, indicating a structural similarity. Components BU-2867T F and G were hydrolyzed with 6N HCl at 110° C. for 16 hours in a sealed tube and the hydrolyzate examined by TLC (n-BuOH-AcOH-H$_2$O=3:1:1 v/v, ninhydrin detection). BU-2867T F afforded the same amino acids (threonine, 4-amino-2-(E)-pentenoic acid and erythro-4-hydroxylysine) as BU-2867T A indicating that it differed from BU-2867T A, B and C only at the fatty acid moieties. All of these fatty acids are considered to be $\alpha, \beta, \gamma, \delta$-unsaturated acids based on the common UV absorption (260 nm) with the parent antibiotics as discussed above. The hydrolyzate of BU-2867T G contained threonine, erythro-4-hydroxylysine but no 4-amino-2-(E)-pentenoic acid. The presence of an unidentified amino acid was indicated by the TLC of the hydrolyzate. This suggested that BU-2867T G differed from the other components at the 4-amino-2-(E)-pentanoic acid moiety. The electron impact mass spectrum (EI-MS) of BU-2867T F did not give the molecular ion but showed a strong fragment ion (base peak) at m/z 151 which was derived from the fatty acid. Acetylation of BU-2867T F in acetic anhydride and pyridine gave the diacetate derivative which gave the molecular ion at m/z 576 along with the fragment ions at m/z 151 (fatty acid) and m/z 284 (acetylcyclic amine). Thus, BU-2867T F was assigned as the decadienoyl analog. It was demonstrated by acid hydrolysis that BU-2867T G differed from other known BU-2867T components at the 4-amino-2-(E)-pentenoic acid moiety. This was corraborated by the $^1$H-NMR spectrum which lacked the doublet methyl signal at δ: 1.27 ppm attributable to 4-amino-2-(E)-pentenoic acid. Upon enzymatic hydrolysis with papain, BU-2867T G afforded an acidic, lipophilic substance (AC-1) and a basic, water soluble substance (BW-1). AC-1 was identified as 2(E), 4(E)-dodecadienoylthreonine by its physico-chemical and spectral data. The chemical ionization mass spectrum (CI-MIS) of BW-1 showed its protonated molecular ion at m/z 258, 16 mass units higher than that of the cyclic amine moiety of BU-2867T A, B and C. Thus, BU-2867T G was concluded to possess 4-amino-5-hydroxy-2-(E)-pentenoic acid in place of 4-amino-2-(E)-pentenoic acid of BU-2867T A. The structures of BU-2867T F and G are shown below:

Structures of BU-2867T F and G

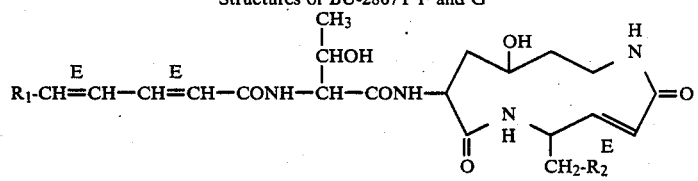

$$R_1-CH=CH-\overset{E}{CH}=CH-CONH-\overset{CH_3}{\underset{CHOH}{CH}}-CONH-\text{[cyclic structure]}$$

| | R$_1$ | R$_2$ |
|---|---|---|
| BU-2867T F | CH$_3$—(CH$_2$)$_4$— | H |
| BU-2867T G | CH$_3$—(CH$_2$)$_6$— | OH |

BIOLOGICAL PROPERTIES

The in vitro minimum inhibitory concentrations of BU-2867T F and G were determined for a number of fungal organisms using the standard tube dilution procedure. The results indicated that the new antibiotics possess antifungal activity. For example, BU-2867T F demonstrated an MIC of 12.5 vs *Candida albicans* A9540, MIC's of 25 vs *Aspergillus fumigatus* strains IAM 2530 and IAM 2034 and an MIC of 12.5 vs *Mucor*

*spinosus* IFO 5317. BU-2867T G showed MIC's of 25 vs *Candida albicans* IAM 4888, *Candida albicans* A9540, *Cryptococcus neoformans* D49, *Cryptococcus neoformans* IAM 4514 and *Trichophyton mentagrophytes* D155, an MIC of 12.5 vs *Aspergillus fumigatus* IAM 2530 and an MIC of 6.3 vs *Aspergillus fumigatus* IAM 2034.

The antitumor activity of BU-2867T F and G was determined in female CDF$_1$ and male BDF$_1$ mice. Lymphocytic leukemia P388 (CDF$_1$ and BDF$_1$ mice) were inoculated by intraperitoneal injection of 0.4 ml diluted ascitic fluid containing 10$^6$ cells per mouse. Test materials were dissolved in 0.9% saline containing 10% dimethylsulfoxide and graded doses of them were administered to mice intraperitoneally 24 hours after tumor implantation. Results are shown below as the increase in median survival time (MST) of test (T) and control (C) animals for various dosage regimens expressed as a percentage ratio. Values for percentage ratios of 125 and above indicate significant antitumor effect.

| Antitumor Activity Against P388 Leukemia | | | |
|---|---|---|---|
| MST (% T/C, gd 1→3, ip*) | | | |
| | 3 | 1 | 0.3 mg/kg |
| BU-2867T F | 127 | 100 | 100 |
| BU-2867T G | 127 | 100 | 100 |

*Treatments given once daily for 3 days

The above data demonstrate that the compounds of the present invention possess inhibitory activity against fungal organisms and mammalian malignant tumors.

According to one aspect of the invention, therefore, there is provided a method for therapeutically treating a mammalian host affected by a fungal infection or by a malignant tumor sensitive to BU-2867T F and/or G which comprises administering to said host an effective antifungal or tumor-inhibiting dose of BU-2867T F and/or G.

In yet another aspect of this invention a pharmaceutical composition is provided which comprises an effective antifungal amount or tumor-inhibiting amount of BU-2867T F and/or G in combination with an inert pharmaceutically acceptable carrier or diluent. These compositions can be made up in any pharmaceutical form appropriate for parenteral administration.

Preparations according to the invention for parenteral administration include sterile aqueous or non-aqueous solutions, suspensions or emulsions. They may also be manufactured in the form of sterile solid compositions which can be dissolved in sterile water, physiological saline or some other sterile injectable medium immediately before use.

It will be appreciated that the actual preferred dosages of the compounds of the present invention will vary according to the particular compound being used, the particular composition formulated, the mode of administration and the particular situs, host and disease being treated. Many factors that modify the action of the drug will be taken into account by those skilled in the art, e.g. age, body weight, sex, diet, time of administration, route of administration, rate of excretion, condition of the host, drug combinations, reaction sensitivities and severity of the disease. Optimal dosages for a given set of conditions can be ascertained by those skilled in the art using conventional dosage determination tests in view of the experimental animal data provided.

The following examples are not intended to be limiting but are illustrative of the invention. Unless otherwise indicated all solvent percentages are by volume.

EXAMPLE 1

FERMENTATION OF ANTIBIOTICS

The stock culture of *Polyangium brachysporum* K481-B101 was propagated at 20° C. for 3 days on agar slant medium composed of 0.5% soluble starch, 0.5% glucose, 0.1% meat extract, 0.1% yeast extract, 0.2% NZ-case (Humko Sheffield Chemical), 0.2% NaCl, 0.1% CaCO$_3$ and 1.6% agar (pH 7.0). A well grown agar slant was used to inoculate the vegetative medium consisting of 2% corn starch, 3% soybean meal, 0.3% MgSO$_4$.7-H$_2$O and 1% CaCO$_3$ (pH 7.0, before sterilization). After incubation at 28° C. for 3 days on a rotary shaker (250 rpm), 5 ml of the growth was transferred into a 500-ml Erlenmeyer flask containing 100 ml of the production medium having the same composition as the vegetative medium.

The antibiotic production was monitored by the paper disc agar diffusion method using *Candida albicans* A9540 as the test organism. The fermentation was continued for 4 days at 28° C. on a rotary shaker and the antibiotic production reached a maximum of 100 mcg/ml.

The fermentation was also carried out in a stir-jar fermenter. A 500-ml portion of the seed culture obtained by flask fermentation was used to inoculate 10 liters of the production medium in a 20-liter vessel. The fermentation was carried out at 28° C. with agitation at 250 rpm and aeration at 10 liters per minutes. The antibiotic production reached a maximum of 150 mcg/ml after forty hours' fermentation.

EXAMPLE 2

Isolation and Purification

The culture broth (230 L) obtained according to the method of Example 1 was extracted by shaking with a mixture of n-butanol (160 L) and methanol (27 L) for one hour. The organic layer was separated with the aid of a Sharpless centrifuge and concentrated to 3.3 L under reduced pressure. The concentrate was poured into 20 L of acetone under vigorous stirring to precipitate the crude antibiotic solid (217 g). A methanolic solution (4 L) of the solid was mixed with 400 g of silica gel (Waco C-200) and the mixture concentrated in vacuo. The silica gel which absorbed the crude antibiotic was placed on the top of a silica gel column (Wako C-200, 4 L) packed with ethyl acetate. The column was developed first with ethyl acetate (6.2 L) and then with ethyl acetate-methanol mixture (8:2, 12.5 L and 5:5, 33.5 L). Subsequent bioactivity (vs *Candida albicans* A9540)-directed fractionation resulted in the isolation of a complex of Bu-2867T as pale yellow solid (114 g). A portion of this solid (31.3 g) was loaded on a column of a reversed phase silica (C$_{18}$, 1 L) which had been equilibrated with 70% aqueous methanol. Elution was carried out with 70% and 80% aqueous methanol and the eluates were pooled on the basis of the bioassay and HPLC (C$_{18}$, 80% aqueous methanol elution). Evaporation of the first pool yielded 3.5 g of semi-pure solid which contained a mixture of components including BU-2867T F and G. The work-up of the second and third pools afforded pure BU-2867T A (4.1 g) and a mixture of BU-2867T A, B and C (10.4 g), respectively as described in USSN 855,649 filed Apr. 25, 1986. Repetition of the above reversed phase chromatography for the rest of the complex sample gave a total of 16.3 g of the minor component mixture (including BU-2867T F and G), 14.6 g of BU-2867T A and 44.6 g of BU-2867T A, B and C mixture. The mixture of BU-2867T F and G (12.7 g) was chromatographed on a column of silica gel (C-200, 700 ml) developing with chloroform-methanol (10:1 and 5:1). The eluate was collected in fractions (18 ml each) which were analyzed by TLC ($C_{18}$, EtOH-$H_2O$=55:45). The initial half of the active fractions (No. 91–160) was pooled, concentrated and lyophilized to afford 1.2 g of white solid which comprised crude BU-2867T F. The latter half was similarly worked up to give 930 mg of crude BU-2867T G. The above BU-2867T F-containing complex (1.20 g) was chromatographed on a reversed phase silica gel (160 ml) with MeOH-$H_2O$ (1:1, 1 L and 5:1, 2.5 L). The first bioactive fractions were pooled, evaporated in vacuo, and lyophilized to give pure BU-2867T F (131 mg). The complex of BU-2867T G (930 mg) obtained above was again chromatographed on a silica gel column (C-200, 190 ml). The elution was carried out by a mixture of $CHCl_3$-MeOH (10:1, 1 L and 5:1, 1.6 L) and the active eluates were pooled and concentrated to give a purer solid containing in admixture with other minor components BU-2867T G (97 mg). This complex was separated by reversed phase silica gel chromatography with aqueous methanol (50%–70%) elution. The first active fractions were pooled and evaporated to give a minor component having very little bioactivity. The second and the third active fractions were similarly worked up to give, respectively, another minor BU-2867T component having insignificant bioactivity and pure BU-2867T G (18.1 mg).

We claim:

1. The process for the preparation of BU-2867T F having the formula

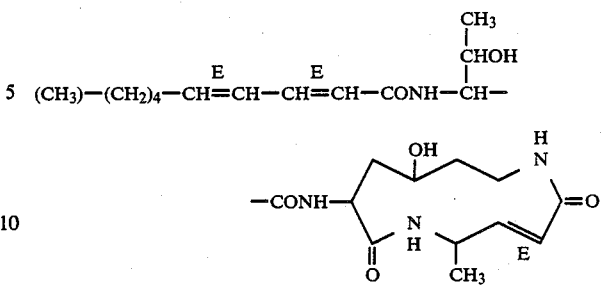

which comprises cultivating *Polyangium brachysporum* (ATCC 53080) or a BU-2867T F-producing mutant thereof in an aqueous nutrient medium containing assimilable sources of carbon and nitrogen under submerged aerobic conditions until a recoverable amount of BU-2867T F is produced by said organism in said culture medium and then recovering the BU-2867T F antibiotic from the culture medium substantially free of co-produced substances.

2. The process for the preparation of BU-2867T G having the formula

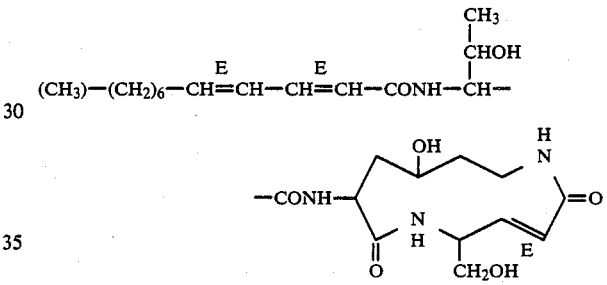

which comprises cultivating a *Polyangium brachysporum* (ATCC 53080) or a BU-2867T G-producing mutant thereof in an aqueous nutrient medium containing assimilable sources of carbon and nitrogen under submerged aerobic conditions until a recoverable amount of BU-2867T G is produced by said organism in said culture medium and then recovering the BU-2867T G antibiotic from the culture medium substantially free of co-produced substances.

* * * * *